United States Patent [19]

Buysch et al.

[11] Patent Number: 5,284,965
[45] Date of Patent: Feb. 8, 1994

[54] PROCESS FOR PREPARING AROMATIC CARBONATES

[75] Inventors: Hans-Josef Buysch; Norbert Schön; Johann Rechner, all of Krefeld, Fed. Rep. of Germany

[73] Assignee: Bayer Aktiengesellschaft, Leverkusen, Fed. Rep. of Germany

[21] Appl. No.: 25,487

[22] Filed: Mar. 3, 1993

[30] Foreign Application Priority Data

Mar. 12, 1992 [DE] Fed. Rep. of Germany ....... 4207853

[51] Int. Cl.$^5$ .................. C07C 69/96; C07C 68/06
[52] U.S. Cl. .................. 558/270; 558/271; 558/273; 558/274
[58] Field of Search ................ 558/270, 274

[56] References Cited

U.S. PATENT DOCUMENTS 4,045,464  8/1977  Romano et al. ............. 558/274
4,182,726  1/1980  Illuminati et al. ............. 558/274 X
4,410,464 10/1983  Hallgren ..................... 558/271

FOREIGN PATENT DOCUMENTS 0461274 12/1991  European Pat. Off.
3308921  9/1983  Fed. Rep. of Germany.

Primary Examiner—Mary C. Lee
Assistant Examiner—Michael G. Ambrose
Attorney, Agent, or Firm—Sprung Horn Kramer & Woods

[57] ABSTRACT

A process is described for preparing aromatic carbonates by transesterification of aliphatic carbonates with phenolic compounds in the presence of titanium compounds known per se, in which, before work-up, the transesterification mixture is cooled to a temperature below 120° C., during which the mixture must remain liquid, the titanium-containing precipitate which is deposited is separated off, and the aromatic carbonate is then obtained by methods which are conventional per se.

11 Claims, No Drawings

PROCESS FOR PREPARING AROMATIC CARBONATES

BACKGROUND OF THE INVENTION

1. Field of the Invention

The present invention relates to a process for preparing aromatic carbonates by transesterification of aliphatic carbonates with phenolic compounds in the presence of titanium compounds. In this process, before work-up, the transesterification mixture is cooled to a temperature below 120° C., during which the mixture must remain liquid, the titanium-containing precipitate which is deposited is separated off, and the aromatic carbonate is obtained by methods which are conventional per se.

2. Description of the Related Art

It is known that alkyl aryl carbonates and diaryl carbonates can be obtained by transesterification of dialkyl carbonates with phenolic compounds, suitable catalysts being titanium compounds. Such catalysed transesterifications are described for example in German Offenlegungsschrift 2 528 412 and German Offenlegungsschrift 2 552 907. Although titanium compounds per se are very suitable catalysts, the selectivity, particularly at long reaction times and high temperatures, leaves something to be desired, as is confirmed for example in EP 879.

It is therefore expedient not to set the degree of conversion at too high a level, since this would require long times at high temperatures; instead, the aim is to work up the transesterification mixture after achieving relatively low to medium degrees of conversion, as is also described in the aforementioned German Offenlegungsschriften.

Such transesterification mixtures have to be worked up in order to obtain the aromatic carbonates. This can be performed for example by distillation or crystallisation. Crystallisations of such mixtures are however complex operations, particularly since a substantial removal of the catalyst must be ensured. A distillative working-up is therefore preferred on account of this requirement. Since high boiling point compounds are to be separated from one another, the whole reaction mixture that is to be worked up again comes within the range of high temperatures combined with long residence times, resulting in secondary reactions, which is just what the low degrees of transesterification were intended to avoid. If on the other hand efforts are made to reduce the distillation temperatures under a very high vacuum, large gas volumes and correspondingly large apparatus combined with high investment must be expected.

The aforementioned difficulties could be avoided if the catalyst responsible for the secondary reactions could be removed from the transesterification mixture before the working-up.

SUMMARY OF THE INVENTION

It has now surprisingly been found that the titanium catalyst can be removed easily, and above all substantially completely, by, before work-up, cooling the reaction mixture to a temperature of below 120° C., preferably below 100° C., especially preferably below 80° C., during which this mixture must remain liquid. The titanium-containing precipitate which is deposited can then be separated off. The remaining reaction mixture contains residual amounts of titanium of less than 100 ppm.

A process has been found for preparating aromatic carbonates of the formula $$R^1O-CO-OR^2 \qquad (I)$$

by transesterification of aliphatic carbonates of the formula $$R^3O-CO-OR^4 \qquad (II)$$

with phenolic compounds of the formula $$R^1OH \qquad (III)$$

in which in the formulae $R^1$ is phenyl or naphthyl, each of which may be mono- to tri-substituted by straight-chain or branched $C_1-C_4$-alkyl, straight-chain or branched $C_1-C_4$-alkoxy, fluorine, chlorine, bromine or cyano, different substituents from the aforementioned range of definitions also being permitted in the case of polysubstitution, $R^2$ represents straight-chain or branched $C_1-C_6$-alkyl or, independently of $R^1$, represents the range of definitions of $R^1$, $R^3$ is straight-chain or branched $C_1-C_6$-alkyl, and $R^4$, independently of $R^2$, has the range of definitions of $R^2$, in the presence of titanium compounds of the formula $$Ti(X^1, X^2, X^3, X^4) \qquad (IV)$$

in which $X^1$, $X^2$, $X^3$ and $X^4$, independently of one another, are halogen, $O-R^5$ or $O-CO-R^5$, $R^5$ representing straight-chain or branched $C_1-C_{18}$-alkyl or the range of definitions mentioned under $R^1$, and in which furthermore $X^3$ and $X^4$ together may be

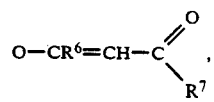

where $R^6$ and $R^7$, independently of one another, are methyl, ethyl or $OR^5$, characterised in that, before work-up, the transesterification mixture is cooled to a temperature of below 120° C., preferably below 100° C., especially preferably below 80° C., during which the mixture must remain liquid, the titanium-containing precipitate which is deposited is separated off, and the aromatic carbonate is obtained by methods which are conventional per se.

DETAILED DESCRIPTION OF THE INVENTION

By means of the cooling, according to the invention, of the reaction mixture and the separation of the titanium-containing precipitate, a reaction mixture is obtained, in a surprisingly simple operation, which can be worked up by crystallisation either distillation or by conditions which are conventional per se in order to obtain the aromatic carbonate, without the danger of any loss of yield. Particular reaction conditions and special precautions, as described above, are not necessary here.

Straight-chain or branched $C_1$-$C_6$-alkyl is for example methyl, ethyl, propyl, isopropyl, butyl, isobutyl or hexyl, preferably methyl or ethyl, and particularly preferably methyl. Higher alkyl within the scope of $R^5$ having 7 to 18 carbon atoms is for example heptyl, octyl, decyl, dodecyl or octadecyl or one of the relevant branched isomers.

Straight-chain or branched $C_1$-$C_4$-alkoxy is for example methoxy, ethoxy, propoxy, isopropoxy, butoxy or isobutoxy.

Suitable phenolic compounds for the process according to the invention are phenol or naphthol or their substitution products, as specified above. The phenolic compound is especially phenol, which may be substituted by $C_1$-$C_3$-alkyl, methoxy, chlorine or bromine; particularly preferably the phenolic compound is the unsubstituted phenol itself. The following phenolic compounds may be mentioned by way of example: phenol, o-, m-, p-cresol, o-, m-, p-ethylphenol, p-isopropylphenol, o-, m-, p-methoxyphenol, o-, m-, p-chlorophenol, bromophenol, cyanophenol, naphthol.

Suitable aliphatic carbonates for the process according to the invention contain at least one aliphatic group; they may therefore be either alkyl carbonates aryl carbonates. Alkyl aryl carbonates are those in which an alkyl radical has already been transesterified by means of one of the aforementioned phenolic compounds, but which are also capable of undergoing a transesterification of the second alkyl group. Dialkyl carbonates are preferably used. These include for example dimethyl carbonate, diethyl carbonate, dipropyl carbonate, diisopropyl carbonate, dibutyl carbonate and diisobutyl carbonate, preferably dimethyl and diethyl carbonates and particularly preferably dimethyl carbonate.

Aromatic carbonates obtainable according to the invention are those containing at least one aromatic group and may accordingly be alkyl aryl carbonates or diaryl carbonates. Alkyl aryl carbonates that may be mentioned by way of example are methyl phenyl carbonate, methyl naphthyl carbonate, ethyl phenyl carbonate, ethyl naphthyl carbonate, methyl chlorophenyl carbonate, methyl methoxyphenyl carbonate and further carbonates that contain alkyl and aryl radicals according to the above description. Diaryl carbonates are for example diphenyl carbonate, dinaphthyl carbonate, phenyl naphthyl carbonate, bis-(chlorophenyl) carbonate, bis-(methoxyphenyl) carbonate, and further carbonates resulting from the above description of the aryl radicals, particular preference however being given to methyl phenyl carbonate and diphenyl carbonate.

It is clear that alkyl aryl carbonates can act both as the reaction product according to formula (I) and as starting material of the formula (II) for the second transesterification. Accordingly the term "transesterification" in the context of the invention includes the following reactions:

a) the transesterification of a dialkyl carbonate with a phenolic compound to form an alkyl aryl carbonate;
b) the transesterification of an alkyl aryl carbonate with a phenolic compound to form a diaryl carbonate;
c) the transesterification of a dialkyl carbonate in a two-stage reaction occurring in the same reactor or in different reactors connected in series, to form the diaryl carbonate via the intermediate stage of the alkyl aryl carbonate; and
d) the transesterification of an alkyl aryl carbonate with a further alkyl aryl carbonate in a disproportionation reaction to form the diaryl carbonate.

In the case of a two-stage reaction according to b) via a), the aryl carbonates may be obtained with two different aryl radicals. However, it is preferred to aim for symmetrical aromatic carbonates on account of the reduced complexity of the reaction and the clear further use of the aromatic carbonates obtained.

In the case of the disproportionation reaction according to d), this disproportionation can be improved in the sense of an extensive isolation of the diaryl carbonate by removing the resultant dialkyl carbonate from the reactor by distillation and thus from the equilibrium. In the case where a disproportionation reaction according to d) takes place in the reactor simultaneously with the transesterifications to the alkyl aryl carbonate and to the diaryl carbonate, any dialkyl carbonate that is obtained in the meantime is in accordance with the invention immediately reinvolved in the transesterification by phenolic compound that is present.

The process according to the invention can of course be carried out batchwise until the desired degree of transesterification is reached, following which the transesterification mixture is cooled according to the invention, separated from the titanium-containing precipitate, and worked up further.

The process according to the invention can however be carried out extremely satisfactorily and continuously in transesterification columns containing suitable internals or packing (cf. EP-A-461 274). In this mode of operation the bottom product is treated according to the invention, i.e. is cooled to a temperature of below 120° C., preferably below 100° C., especially preferably below 80° C., during which this bottom product must remain liquid, is separated from the titanium-containing precipitate which is deposited, and is then worked up further.

Suitable titanium compounds for the process according to the invention are those of the above formulae (IV), for example titanium tetrachloride, titanium tetraisopropylate, titanium tetrabutylate, titanium tetradodecylate, titanium tetraphenolate, titanium tetramethoxyphenolate, titanium tetrachlorophenolate, titanium tetraacetate, titanium tetrabutyrate, titanium tetrabenzoate, titanium tetraoctoate, titanium-IV-acetylacetonate diisopropylate, titanium-IV-acetylacetonate dibutylate, preferably titanium tetrachloride, titanium tetraisopropylate, titanium tetrabutylate, titanium tetradodecylate and titanium tetraphenolate. Such titanium catalysts are known to the person skilled in the art.

The amounts used and the molar ratios of the starting products and catalyst are chosen in the manner known to the person skilled in the art from the prior art, for example according to German Offenlegungsschrift 2 528 412, German Offenlegungsschrift 2 552 907, EP 879, EP 880 and EP-A-461 274; the same comments apply similarly to the temperatures and pressures to be used for the transesterification.

The separation according to the invention of the titanium compounds from the reaction mixture is generally performed by first of all cooling the transesterification mixture to a temperature of below 120° C., preferably below 100° C., especially preferably below 80° C. In cases of low melting, not substituted aryl carbonates or in cases of a high amount of phenol in the reaction mixture, the reaction mixture may be cooled advantageously even below 60° C., and particularly preferably below 50° C. The transesterification mixture is kept liquid during this time, which, depending on the composition, requires another lowest temperature, which however can easily be determined by preliminary experiments in the particular case.

The titanium-containing precipitate which is deposited during cooling can be separated from the transesterification mixture by conventional techniques, for example sedimentation, filtration or centrifugation.

The liquid state and a suitable viscosity of the transesterification mixture can be achieved by setting the degree of transesterification so that sufficient phenol and/or aliphatic carbonate, preferably dialkyl carbonate, is still present in the transesterification mixture. The liquid state and a suitable viscosity can however also be set by subsequent addition of phenolic compounds and/or aliphatic carbonate. Finally, it is also possible to add a foreign, inert solvent. Obviously it is also possible to use a plurality of compounds from the group comprising phenolic compound, aliphatic carbonate and inert solvent. Inert solvents, in other words solvents that are not reactive under the conditions of the separation of the titanium-containing precipitate which is deposited and of the subsequent working-up, are known to the person skilled in the art and are for example cyclohexane, pentane, hexane, octane, isooctane, isononane, benzene, toluene, xylene, cumene, cymol and mesitylene, and also diisopropyl ether, methyl tert-butyl ether, methyl tertamyl ether, dibutyl ether, and other inert solvents.

The composition of the transesterification mixture before the separation of the titanium-containing precipitate which is deposited may vary within wide limits depending on the setting of the degree of conversion and may for example have the following composition:
95 to 10% by weight of phenolic compound,
0 to 50% by weight of dialkyl carbonate,
0 to 80% by weight of alkyl aryl carbonate, and
0.2 to 90% by weight of diaryl carbonate,
the sum of alkyl aryl carbonate and diaryl carbonate being at least 5% by weight.

Before the separation of the titanium-containing precipitate which is deposited, the transesterification mixture preferably has the following composition:
90 to 16% by weight of phenolic compound,
0 to 30% by weight of dialkyl carbonate,
4 to 50% by weight of alkyl aryl carbonate, and
1 to 60% by weight of diaryl carbonate;
the sum of alkyl aryl carbonate and diaryl carbonate being at least 8% by weight, and particularly preferably
85 to 30% by weight of phenolic compound,
0 to 20% by weight of dialkyl carbonate,
6 to 40% by weight of alkyl aryl carbonate, and
2 to 40% by weight of diaryl carbonate,
the sum of alkyl aryl carbonate and diaryl carbonate being at least 10% by weight.

These figures refer to the total weight of the transesterification mixture to be worked up, excluding the titanium compound.

In the case where one of the aforementioned inert solvents is used in addition, the amount thereof is 3 to 50% by weight, preferably 5 to 30% by weight, based on the sum of the weights of the transesterification mixture and solvent employed. The compositions of the transesterification mixture illustrate the alternative possible ways in which the transesterification can be directed preferentially to the alkyl aryl carbonate or preferentially to the diaryl carbonate. In all the abovementioned cases an effective separation of the catalyst is possible in the manner according to the invention so that the content of titanium catalyst in the reaction (transesterification) mixture freed from said titanium catalyst is less than 100 ppm, preferably less than 50 ppm, and particularly preferably less than 20 ppm.

Furthermore, it is possible to precipitate and thereby purify the titanium catalyst after removal of the unreacted starting products and aromatic carbonate by adding one or more phenolic compounds in amounts of 0.5 to 20 parts by weight, based on the amount of catalyst used.

The titanium-containing precipitate separated off can be recycled without further purification into the transesterification reaction. For this purpose it can be used as such or after dissolution in the starting products. It is of course also possible to remove from the transesterification process all or some of the titanium-containing precipitate which has been separated off and to replace it by fresh catalyst. This depends, in a manner that is known in principle to the person skilled in the art, on the actual degree of contamination or deactivation of the catalyst. However, long service lives of the catalystare possible thanks to the gentler treatment of the catalyst under the measures according to the invention, where high temperatures and long times are avoided.

EXAMPLE 1

Transesterification and separation of a catalyst

A mixture of 250 g of phenol and 3.77 g of titanium tetraisopropylate was added per hour to the head of a 10-tray bubble-cap column 60 cm long and 5 cm in diameter after stationary equilibrium had been reached, and at the same time 250 g of dimethyl carbonate in vapour form were metered in per hour at the foot of the column. The column jacket and bottom were kept at 180° C., the dimethyl carbonate vaporiser at 190° C., and the dephlegmator at the head of the column at 87° C. The internal temperature of the column was 165° to 170° C. 250 to 270 g of product mixture of approximately the following composition were removed per hour from the bottom of the column:
84% by weight of phenol
12% by weight of methyl phenyl carbonate
4% by weight of diphenyl carbonate After 4 hours' running time the product fractions were combined and the combined mixture was cooled to 50° C., whereupon a precipitate was immediately deposited, which was separated by filtration through a pressure filter. The clear filtrate contained less than 5 ppm Ti; the initial amount was 3600 ppm Ti.

The filter residue was re-used corresponding to the above example, the same esterification result being obtained.

EXAMPLE 2

Recovery of the catalyst from the bottom of a distillation column

Example 1 was repeated, 1075 g of a product mixture comprising
85% by weight of phenol,
12% by weight of methyl phenyl carbonate,
3% by weight of diphenyl carbonate, and the titanium catalyst
being removed over a period of 4 hours from the bottom of the column. The product mixture was distilled over a 40 cm long column packed with Raschig rings at 25 to 0.1 mbar. The phenol, methyl phenyl carbonate and greater proportion of the diphenyl carbonate were separated via the head of the column. 30.5 g of a brown, glassy mass remained behind as bottom product (titanium content 8.3% by weight, 53 mmol). 100 g of phenol were added to this oil and the mixture was stirred for 15 minutes at about 60° C. Orange crystals then formed, which were isolated, washed once with 50 g of phenol at 45° to 50° C., and dried in vacuo. 24.9 g of a titanium compound containing 9.2% by weight of titanium were obtained. This corresponds to 90.3% of the titanium used. the catalyst recovered in this way was re-used as described in Example 1 with the titanium concentration employed in this example, the same transesterification result was the case as being obtained there.

What is claimed is:

1. A process for preparing an aromatic carbonate of the formula

by transesterification of an aliphatic carbonate of the formula

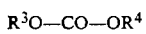

with a phenolic compound of the formula

in which the formulae
  $R^1$ is phenyl or naphthyl, each of which may be mono- to tri-substituted by straight-chain or branched $C_1$-$C_4$-alkyl, straight-chain or branched $C_1$-$C_4$-alkoxy, fluorine, chlorine, bromine or cyano, different substituents from the aforementioned range of definitions also being permitted in the case of polysubstitution,
  $R^2$ represents straight-chain or branched $C_1$-$C_6$-alkyl or, independently of $R^1$, represents the range of definitions of $R^1$,
  $R^3$ is straight-chain or branched $C_1$-$C_6$-alkyl, and
  $R^4$, independently of $R^2$, has the range of definitions of $R^2$,
in the presence of a titanium compound of the formula

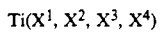

in which
  $X^1$, $X^2$, $X^3$ and $X^4$, independently of one another, are halogen, O—$R^5$ or O—CO—$R^5$, $R^5$ representing straight-chain or branched $C_1$-$C_{18}$-alkyl or the range of definitions mentioned under $R^1$, and in which furthermore $X^3$ and $X^4$ together may be

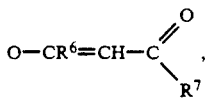

where $R^6$ and $R^7$, independently of one another, are methyl, ethyl or O$R^5$,
wherein, before work-up, the transesterification mixture is cooled to a temperature of below 120° C., during which the mixture must remain liquid, the titanium-containing precipitate which is deposited is separated off, and the aromatic carbonate is obtained by methods per se which are conventional.

2. The process of claim 1, wherein the transesterification mixture is cooled to a temperature of below 100° C.

3. The process of claim 2, wherein the transesterification mixture is cooled to a temperature of below 80° C.

4. The process of claim 3, wherein the transesterification mixture is cooled to a temperature of below 60° C.

5. The process of claim 4, wherein the transesterification mixture is cooled to a temperature of below 50° C.

6. The process of claim 1, wherein the liquid state is maintained by the presence or addition of phenolic compound, aliphatic carbonate, inert solvent or a mixture of a plurality thereof.

7. The process of claim 6, wherein the following composition of the transesterification mixture is maintained or set:
  95 to 10% by weight of phenolic compound,
  0 to 50% by weight of dialkyl carbonate,
  0 to 80% by weight of alkyl aryl carbonate, and
  0.2 to 90% by weight of diaryl carbonate,
the sum of alkyl aryl carbonate and diaryl carbonate being at least 5% by weight, the weight percentage figures being based on the total weight of the transesterification mixture to be worked up, excluding the titanium compound.

8. The process of claim 7, wherein the following composition of the transesterification mixture is maintained or set:
  90 to 16% by weight of phenolic compound,
  0 to 30% by weight of dialkyl carbonate,
  4 to 50% by weight of alkyl aryl carbonate, and
  1 to 60% by weight of diaryl carbonate,
the sum of alkyl aryl carbonate and diaryl carbonate being at least 8% by weight, the weight percentage figures being based on the total weight of the transesterification mixture to be worked up, excluding the titanium compound.

9. The process of claim 8, wherein the following composition of the transesterification mixture is maintained or set:
  85 to 30% by weight of phenolic compound,
  0 to 20% by weight of dialkyl carbonate,
  6 to 40% by weight of alkyl aryl carbonate, and
  2 to 40% by weight of diaryl carbonate,
the sum of alkyl aryl carbonate and diaryl carbonate being at least 10% by weight, the weight percentage figures being based on the total weight of the transesterification mixture to be worked up, excluding the titanium compound.

10. The process of claim 1, wherein the separated, titanium-containing precipitate is recycled as titanium compound into the transesterification.

11. The process of claim 1, wherein first of all the unreacted starting products and the aromatic carbonates are separated off by methods per se which are conventional and then the remaining catalyst is purified and recovered by adding at least one phenolic compound.

* * * * *